(12) United States Patent
Takemoto et al.

(10) Patent No.: US 10,261,055 B2
(45) Date of Patent: Apr. 16, 2019

(54) PROBE, ULTRASONIC TESTING APPARATUS, AND ULTRASONIC TESTING CONTROL METHOD

(71) Applicant: MITSUBISHI HEAVY INDUSTRIES, LTD., Minato-ku, Tokyo (JP)

(72) Inventors: Hiroshi Takemoto, Tokyo (JP); Mitsuyoshi Uematsu, Tokyo (JP); Seiichi Kawanami, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 227 days.

(21) Appl. No.: 15/025,555

(22) PCT Filed: Sep. 3, 2014

(86) PCT No.: PCT/JP2014/073254
§ 371 (c)(1),
(2) Date: Mar. 29, 2016

(87) PCT Pub. No.: WO2015/053014
PCT Pub. Date: Apr. 16, 2015

(65) Prior Publication Data
US 2016/0238567 A1    Aug. 18, 2016

(30) Foreign Application Priority Data

Oct. 7, 2013 (JP) .................................. 2013-210516

(51) Int. Cl.
*G01N 29/26* (2006.01)
*B06B 1/06* (2006.01)
(Continued)

(52) U.S. Cl.
CPC ......... *G01N 29/262* (2013.01); *B06B 1/0629* (2013.01); *G01N 29/2456* (2013.01); *G10K 11/346* (2013.01); *G01N 2291/106* (2013.01)

(58) Field of Classification Search
None
See application file for complete search history.

(56) References Cited

U.S. PATENT DOCUMENTS 3,911,730 A * 10/1975 Niklas ................ G01N 29/0645
                                                                    73/619
5,995,453 A    11/1999 Hirata
(Continued)

FOREIGN PATENT DOCUMENTS

EP      0908241 A2    4/1999
JP      2-26545 A     1/1990
(Continued)

OTHER PUBLICATIONS

International Search Report dated Dec. 2, 2014, in International Application No. PCT/JP2014/073254.
(Continued)

*Primary Examiner* — Xin Y Zhong
(74) *Attorney, Agent, or Firm* — Hauptman Ham, LLP

(57) ABSTRACT

A probe provided with a transceiving surface longer in a length direction than in a width direction thereof, and an array of ultrasonic elements provided on the transceiving surface, the probe being for emitting ultrasonic waves to a surface to be inspected of an object to be inspected that faces the transceiving surface, while moving in the width direction, the ultrasonic elements being shaped so as to have the same length in the length direction and in the width direction, and the certain of ultrasonic elements being aligned in the length direction and in the width direction and emitting ultrasonic waves a large number of times throughout the length direction in predetermined emission units of one or more ultrasonic elements.

6 Claims, 5 Drawing Sheets

(51) Int. Cl.
*G10K 11/34* (2006.01)
*G01N 29/24* (2006.01)

(56) References Cited

U.S. PATENT DOCUMENTS

| | | | | |
|---|---|---|---|---|
| 7,927,280 | B2* | 4/2011 | Davidsen | G01S 7/5208 |
| | | | | 600/447 |
| 2003/0055308 | A1* | 3/2003 | Friemel | A61B 8/14 |
| | | | | 600/15 |
| 2011/0126626 | A1 | 6/2011 | Koch et al. | |
| 2014/0083193 | A1* | 3/2014 | Inagaki | G01N 29/069 |
| | | | | 73/629 |
| 2016/0025684 | A1* | 1/2016 | Deneuville | G01N 29/225 |
| | | | | 73/622 |

FOREIGN PATENT DOCUMENTS

| JP | 5-312792 A | 11/1993 |
|---|---|---|
| JP | 11-187492 A | 7/1999 |
| JP | 2001-108661 A | 4/2001 |
| JP | 2004-33666 A | 2/2004 |
| JP | 3505296 B2 | 3/2004 |
| JP | 2007-301023 A | 11/2007 |
| JP | 2008-301903 A | 12/2008 |
| JP | 2012-117825 A | 6/2012 |
| JP | 2015-62453 A | 4/2015 |

OTHER PUBLICATIONS

Written Opinion in International Patent Application No. PCT/JP2014/073254, dated Feb. 12, 2014.

Extended European Search Report in EP Application No. 14852961.3, dated Jul. 14, 2016.

Office Action in JP Application No. 2013-210516, dated Jun. 6, 2017.

* cited by examiner

PROBE, ULTRASONIC TESTING APPARATUS, AND ULTRASONIC TESTING CONTROL METHOD

TECHNICAL FIELD

The present invention pertains to a probe that emits ultrasonic waves to an object to be inspected and receives ultrasonic waves reflected by the object to be inspected, to an ultrasonic testing apparatus, and to an ultrasonic testing control method.

BACKGROUND ART

Conventionally, ultrasonic probes having an array of piezoelectric transducers arranged in an array are known examples of probes that emit ultrasonic waves (see Patent Literature 1, for example). In such ultrasonic probes, the array of piezoelectric transducers are arranged at a predetermined pitch in the array direction.

CITATION LIST

Patent Literature

Patent Literature 1: Japanese Patent No. 3505296B

SUMMARY OF INVENTION

Technical Problem

However, in the ultrasonic probe of Patent Document 1, if the surface to be inspected of the object to be inspected is inclined at one ultrasonic element among an array of ultrasonic elements (piezoelectric transducers) arranged in an array direction, and specifically, if there is a large difference in height between one side and the other side of the surface to be inspected in the slicing direction, which is orthogonal to the array direction of one ultrasonic element, then the distance between the ultrasonic element and the surface to be inspected varies in the slicing direction, which can result in a false response in test results obtained by an ultrasonic testing. In particular, if the object to be inspected having the surface to be inspected is made of a material having acoustic anisotropy, then if the variation in distance results in the emission direction of the ultrasonic waves varying, this results in variation in ultrasonic waves propagating inside the object to be inspected, which increases the probability of a false response occurring.

An object of the present invention is to provide a probe, an ultrasonic testing apparatus, and an ultrasonic testing control method by which ultrasonic waves can be stably emitted even if the surface to be inspected of the object to be inspected is inclined with respect to the transceiving surface of the probe.

Solution to Problem

A probe of the present invention includes: a transceiving surface that has a greater length in a length direction than in a width direction; and an array of ultrasonic elements provided on the transceiving surface. The probe emits ultrasonic waves, while moving in the width direction, to a surface to be inspected of an object to be inspected, the surface to be inspected facing the transceiving surface. Each of the ultrasonic elements is formed in a shape so as to have a same length in the length direction and the width direction. The array of ultrasonic elements are arranged in the length direction and the width direction, and the probe emits, throughout the length direction, ultrasonic waves an array of times in a predetermined emission unit corresponding to one or more of the ultrasonic elements.

According to this configuration, it is possible to form the ultrasonic elements having the same length in the length direction and the width direction, and thus, even if the surface to be inspected facing the ultrasonic elements is inclined, it is possible to achieve a small difference in height between one end and the other end in the width direction. As a result, it is possible to reduce variation in distance between the ultrasonic element and the surface to be inspected in the width direction, and to stably emit ultrasonic waves to the surface to be inspected. Shapes in which the length direction and width direction lengths are the same include, for example, polygons such as squares, or circles.

It is preferable that the array of ultrasonic elements include a first ultrasonic element group arranged in one row in the length direction, and a second ultrasonic element group arranged in one row in the length direction, the second ultrasonic element group being adjacent in the width direction to the first ultrasonic element group. It is also preferable that each of the ultrasonic elements in the first ultrasonic element group be positioned between the ultrasonic elements in the second ultrasonic element group that are adjacent to each other in the length direction and that the emission unit correspond to each of the ultrasonic elements.

According to this configuration, in the emission unit corresponding to each of the ultrasonic elements, the ultrasonic elements in the first ultrasonic element group and the ultrasonic elements in the second ultrasonic element group can alternately emit ultrasonic waves in the length direction. At this time, each of the ultrasonic elements in the first ultrasonic element group is positioned between the ultrasonic elements in the second ultrasonic element group that are adjacent to each other in the length direction. Thus, ultrasonic waves can be emitted at a shorter interval than between the ultrasonic elements in the ultrasonic element groups, enabling precise ultrasonic wave flaw detection in the length direction.

It is preferable that the array of ultrasonic elements be arranged in a matrix in the length direction and the width direction. It is also preferable that the emission unit be an ultrasonic element emission group defined by an array of the ultrasonic elements adjacent to each other in the length direction and an array of the ultrasonic elements adjacent to each other in the width direction and having the same number of the ultrasonic elements in the length direction and the width direction.

According to this configuration, it is possible to emit ultrasonic waves in the length direction in the emission unit corresponding to the ultrasonic element emission group. In this manner, the ultrasonic element emission group enables an increase in acoustic pressure compared a case in which ultrasonic waves are emitted from one ultrasonic element, enabling more stable emission of ultrasonic waves, and enabling the ultrasonic waves reflected by the object to be inspected to be more suitably received.

It is preferable that the array of ultrasonic elements be arranged in a matrix at a predetermined inclination with respect to the length direction and the width direction. It is also preferable that the emission unit correspond to an ultrasonic element emission group defined by an array of the ultrasonic elements adjacent to each other in the length direction and an array of the ultrasonic elements adjacent to each other in the width direction and having the same number of the ultrasonic elements in the length direction and the width direction.

According to this configuration, it is possible to emit ultrasonic waves in the length direction in the emission unit corresponding to the ultrasonic element emission group. In this manner, the ultrasonic element emission group makes it possible to increase acoustic pressure compared a case in which ultrasonic waves are emitted from one ultrasonic element, enabling more stable emission of ultrasonic waves, and enabling the ultrasonic waves reflected by the object to be inspected to be more suitably received.

It is preferable that, with respect to ultrasonic waves emitted from at least one of the ultrasonic elements, the ultrasonic element emission group cause ultrasonic waves emitted from the other ultrasonic elements to be delayed, thereby focusing ultrasonic waves on a predetermined focal point position in a depth direction that is orthogonal to the surface to be inspected.

According to this configuration, changing emission timings for ultrasonic waves emitted from the array of ultrasonic elements in the ultrasonic element emission group enables so-called electronic focusing in which the ultrasonic waves are focused on a predetermined focal point position. Thus, focusing the ultrasonic waves in this manner makes it possible to increase acoustic pressure and improve resolution, enabling improvement in sensitivity in ultrasonic flaw detection.

An ultrasonic testing apparatus of the present invention includes the above-mentioned probe; and a control unit that controls the probe. In the emission unit corresponding to each of the ultrasonic elements, the control unit emits ultrasonic waves a large number of times while changing a position of the emission unit in the length direction from one end toward the other end in the length direction such that the ultrasonic elements in the first ultrasonic element group alternate with the ultrasonic elements in the second ultrasonic element group.

According to this configuration, the control unit emits ultrasonic waves a large number of times in the length direction of the probe, enabling the ultrasonic waves to be emitted at a shorter interval than between the ultrasonic elements in the ultrasonic element groups. As a result, it is possible to perform precise ultrasonic flaw detection in the length direction.

Another ultrasonic testing apparatus of the present invention includes the above-described probe; and a control unit that controls the probe. In the emission unit corresponding to the ultrasonic element group, the control unit emits ultrasonic waves a large number of times while changing a position of the emission unit in the length direction from one end toward the other end in the length direction such that the respective portions of the emission units overlap.

According to this configuration, the control unit emits ultrasonic waves a large number of times in the length direction of the probe with the respective portions of the emission units overlapping, enabling the ultrasonic waves to be emitted at a short interval. As a result, it is possible to perform precise ultrasonic flaw detection in the length direction.

It is preferable that, with the emission unit corresponding to the ultrasonic element emission group, the control unit simultaneously excite the certain of ultrasonic elements in the ultrasonic element emission group to emit ultrasonic waves from the array of ultrasonic elements, and it is more preferable that, wherein the certain ultrasonic elements receive ultrasonic waves reflected by the object to be inspected.

According to this configuration, the control unit simultaneously excite the certain of ultrasonic elements in the ultrasonic element emission group to emit. This makes it possible to increase acoustic pressure compared a case in which ultrasonic waves are emitted from one ultrasonic element, enabling more stable emission of ultrasonic waves. Furthermore, the ultrasonic waves can be received by the respective ultrasonic elements, and thus, resolution can be improved for receiving the ultrasonic waves reflected by the object to be inspected.

It is preferable that, if simultaneously exciting the certain of ultrasonic elements in the ultrasonic element emission group, the control unit perform delay control to delay ultrasonic waves emitted from the other ultrasonic elements.

According to this configuration, changing emission timings for ultrasonic waves emitted from the certain of ultrasonic elements in the ultrasonic element emission group enables so-called electronic focusing in which the ultrasonic waves are focused on a predetermined focal point position. Thus, focusing the ultrasonic waves makes it possible to increase acoustic pressure and improve resolution, enabling improvement in sensitivity in ultrasonic flaw detection.

An ultrasonic testing control method of the present invention is a method for controlling a probe. The probe includes a transceiving surface that has a greater length in a length direction than in a width direction, and an array of ultrasonic elements provided on the transceiving surface. The probe emits ultrasonic waves to a surface to be inspected of an object to be inspected, the surface to be inspected facing the transceiving surface, while moving in the width direction. Each of the ultrasonic elements is formed in a shape so as to have the same length in the length direction and the width direction. The array of ultrasonic elements include a first ultrasonic element group arranged in one row in the length direction, and a second ultrasonic element group arranged in one row in the length direction, the second ultrasonic element group being adjacent in the width direction to the first ultrasonic element group. Each of the ultrasonic elements in the first ultrasonic element group is positioned between the ultrasonic elements in the second ultrasonic element group that are adjacent to each other in the length direction. The method includes, in an emission unit corresponding to each of the ultrasonic elements, emitting ultrasonic waves a large number of times while changing a position of the emission unit in the length direction from one end toward the other end in the length direction such that the ultrasonic elements in the first ultrasonic element group alternate with the ultrasonic elements in the second ultrasonic element group.

According to this configuration, it is possible to form the ultrasonic elements having the same length in the length direction and the width direction, and thus, it is possible to achieve a small difference in height between one end and the other end in the width direction and to stably emit ultrasonic waves to the surface to be inspected. At this time, the control unit emits ultrasonic waves a large number of times in the length direction of the probe, enabling ultrasonic waves to be emitted at a shorter interval than between the ultrasonic elements in the ultrasonic element groups. As a result, it is possible to perform precise ultrasonic flaw detection in the length direction.

Another ultrasonic testing control method of the present invention is a method for controlling a probe. The probe includes a transceiving surface that has a greater length in a length direction than in a width direction, and an array of ultrasonic elements provided on the transceiving surface. The probe emits ultrasonic waves to a surface to be inspected of an object to be inspected, the surface to be inspected facing the transceiving surface, while moving in the width direction. Each of the ultrasonic elements is formed in a shape so as to have the same length in the length direction and the width direction. The array of ultrasonic elements are arranged in a matrix in the length direction and the width direction, The method includes, in an emission unit corresponding to an ultrasonic element emission group defined by an array of the ultrasonic elements adjacent to each other in the length direction and an array of the ultrasonic elements adjacent to each other in the width direction and having the same number of the ultrasonic elements in the length direction and the width direction, emitting ultrasonic waves a large number of times while changing a position of the emission unit in the length direction from one end toward the other end in the length direction such that the respective portions of the emission units overlap.

According to this configuration, it is possible to form the ultrasonic elements having the same length in the length direction and the width direction, and thus, it is possible to achieve a small difference in height between one end and the other end in the width direction and to stably emit ultrasonic waves to the surface to be inspected. At this time, the control unit emits ultrasonic waves a large number of times in the length direction of the probe with the respective portions of the emission units overlapping, enabling the ultrasonic waves to be emitted at a short interval. As a result, it is possible to perform precise ultrasonic flaw detection in the length direction.

Another ultrasonic testing control method of the present invention is a method for controlling a probe. The probe includes a transceiving surface that has a greater length in a length direction than in a width direction, and an array of ultrasonic elements provided on the transceiving surface. The probe emits ultrasonic waves to a surface to be inspected of an object to be inspected, the surface to be inspected facing the transceiving surface, while moving in the width direction. Each of the ultrasonic elements is formed in a shape so as to have the same length in the length direction and the width direction. The array of ultrasonic elements is arranged in a matrix at a predetermined inclination with respect to the length direction and the width direction. The method includes, in an emission unit corresponding to an ultrasonic element emission group defined by an array of the ultrasonic elements adjacent to each other in the length direction and an array of the ultrasonic elements adjacent to each other in the width direction and having the same number of the ultrasonic elements in the length direction and the width direction, emitting ultrasonic waves a large number of times while changing a position of the emission unit in the length direction from one end toward the other end in the length direction such that the respective portions of the emission units overlap.

According to this configuration, it is possible to form the ultrasonic elements having the same length in the length direction and the width direction, and thus, it is possible to achieve a small difference in height between one end and the other end in the width direction and to stably emit ultrasonic waves to the surface to be inspected. At this time, the control unit emits ultrasonic waves a large number of times in the length direction of the probe with the respective portions of the emission units overlapping, enabling the ultrasonic waves to be emitted at a short interval. As a result, it is possible to perform precise ultrasonic flaw detection in the length direction.

DESCRIPTION OF EMBODIMENTS

Detailed description will be given below of embodiments according to the present invention on the basis of the drawings. Note that the present invention is not limited by these embodiments. In addition, the constituent elements in the embodiments described below include those that can be easily replaced by a person skilled in the art or those that are substantially the same.

First Reference Example

Figure 1:
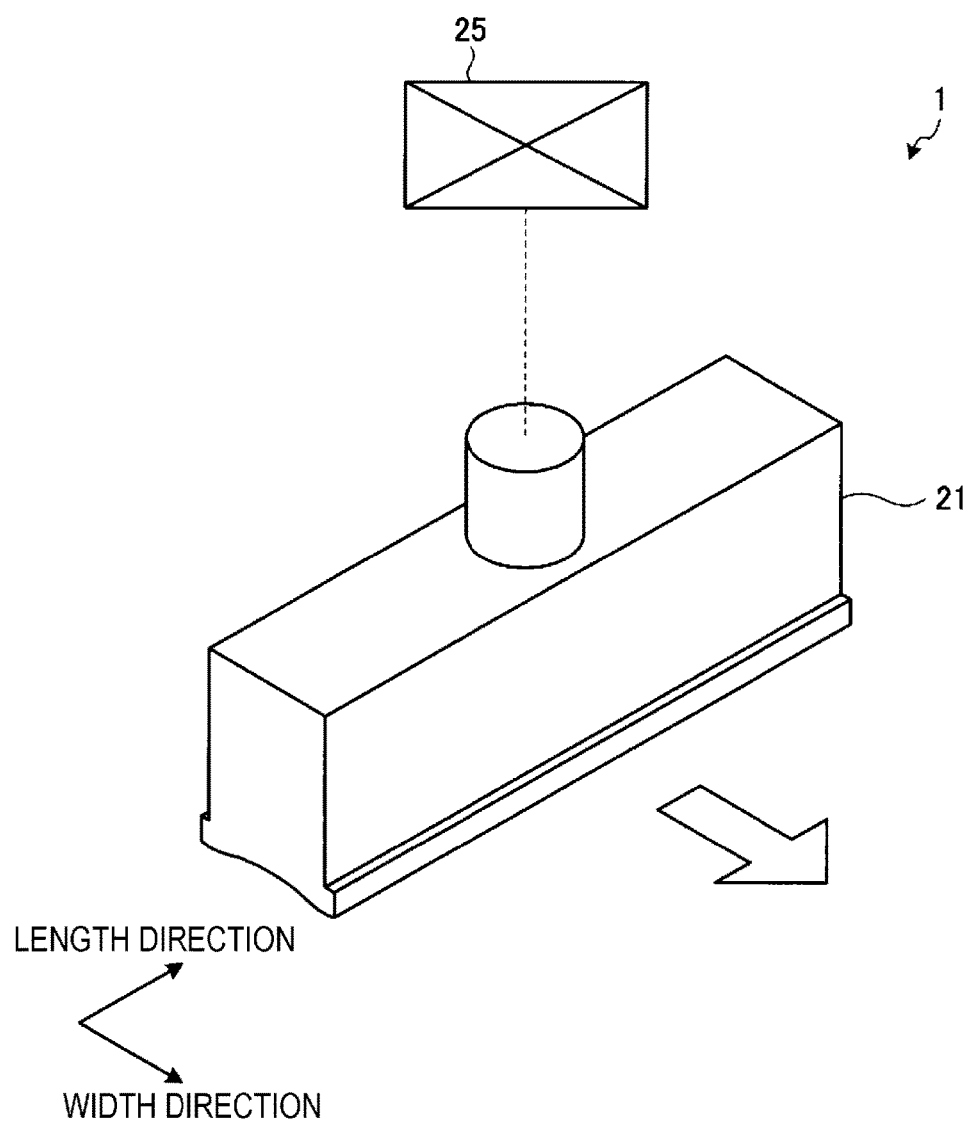
FIG. 1 is a schematic configuration diagram schematically illustrating an ultrasonic testing apparatus according to at least one embodiment.
Figure 2:
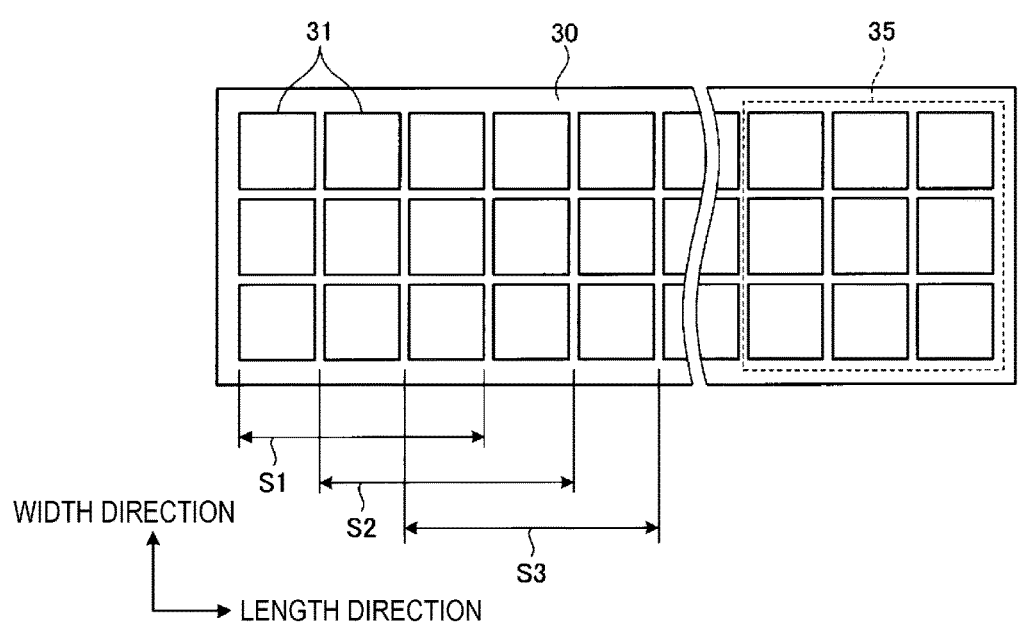
FIG. 2 is a schematic diagram illustrating a transceiving surface of a probe of the ultrasonic testing apparatus according to a first reference example.
Figure 3:
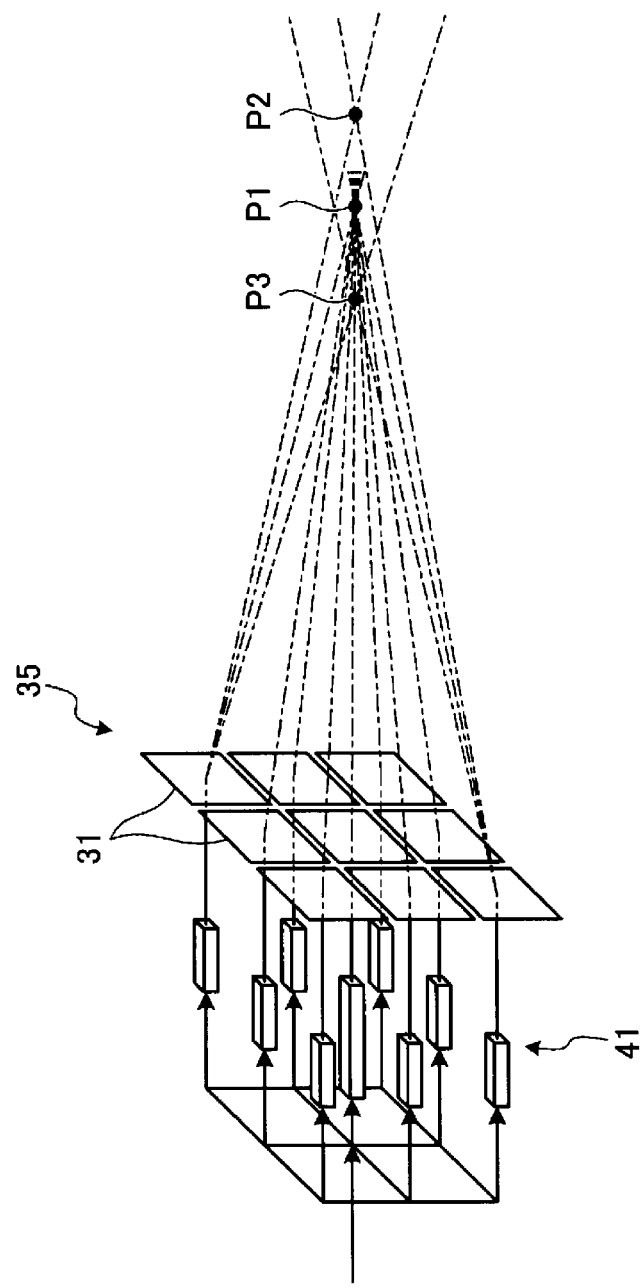
FIG. 3 is a descriptive diagram pertaining to delay control for the ultrasonic testing apparatus according to the first reference example.

FIG. 1 is a schematic configuration diagram schematically illustrating an ultrasonic testing apparatus according to the first reference example, and FIG. 2 is a schematic diagram illustrating a transceiving surface of a probe of the ultrasonic testing apparatus according to the first reference example. FIG. 3 is a descriptive diagram pertaining to delay control for the ultrasonic testing apparatus according to the first reference example.

An ultrasonic testing apparatus 1 of the first reference example causes an ultrasonic probe 21 (hereinafter simply referred to as a "probe") to move along a surface to be inspected of an object to be inspected while emitting ultrasonic waves to the surface to be inspected from the probe 21 to detect flaws in and inspect the object to be inspected under the surface to be inspected. The object to be inspected is made of a composite material, for example, and carbon fiber-reinforced plastic (CFRP) is used as such a composite material. In the present embodiment, the object to be inspected is made of CFRP, but there is no special limitation on the material thereof, and another type of fiber-reinforced plastic or a metal material such as an aluminum alloy may be used.

The composite material has acoustic anisotropy, and is prone to causing variation in the sound velocity of the ultrasonic waves, and the like depending on the propagation direction of the ultrasonic waves emitted to the object to be inspected. As a result, the error in inspection results obtained by flaw detection becomes large. Thus, if the object to be inspected is made of a material having acoustic anisotropy, it is preferable that the emission direction in which the ultrasonic waves are emitted to the object to be inspected be a fixed emission direction.

Next, the ultrasonic testing apparatus 1 will be described with reference to FIG. 1. As illustrated in FIG. 1, the ultrasonic testing apparatus 1 includes the probe 21 and a control unit 25.

The probe 21 includes a transceiving surface 30 that emits ultrasonic waves toward a surface to be inspected of the object to be inspected, and receives reflected ultrasonic waves. As illustrated in FIG. 2, the transceiving surface 30 is long in the length direction, and the length thereof in the width direction is shorter than in the length direction. The probe 21 moves in the width direction of the transceiving surface 30 with the transceiving surface 30 facing the surface to be inspected.

The probe 21 is of a matrix array type, and is provided with an array of ultrasonic elements 31 arranged in the length direction and the width direction on the transceiving surface 30. Each ultrasonic element 31 has a piezoelectric element, and can emit ultrasonic waves as well as receive ultrasonic waves. Additionally, each ultrasonic element 31 is formed such that lengths in the length direction and width direction thereof are the same, and the ultrasonic elements 31 have a square shape in the first reference example. In the first reference example, the ultrasonic elements 31 have a square shape, but may have a circular shape or any shape as long as the lengths in the length direction and width direction are the same. "Same length" may mean substantially the same length, and the lengths need only be the same to the degree that it is possible to stably emit ultrasonic waves toward the surface to be inspected. The array of ultrasonic elements 31 are arranged such that a group of the ultrasonic elements 31 that are arranged in one row in the length direction is arranged in three rows in the width direction, for example. The probe 21 emits, throughout the length direction, ultrasonic waves a large number of times in a predetermined emission unit.

The emission unit is an ultrasonic element emission group 35 surrounded by the dotted line in FIG. 2. The ultrasonic element emission group 35 is constituted of a total of nine ultrasonic elements 31: three ultrasonic elements 31 adjacent to each other in the length direction by three ultrasonic elements 31 adjacent to each other in the width direction. If ultrasonic waves are emitted with such an ultrasonic element emission group 35 as the emission unit, then the probe 21 emits ultrasonic waves a large number of times while changing the position of the emission unit in the length direction from one end to the other end in the length direction with the respective portions of the emission units overlapping.

Specifically as illustrated in FIG. 2, the first emission unit as the ultrasonic element emission group 35 is designated as S1, the second emission unit as the ultrasonic element emission group 35 is designated as S2, and the third emission unit as the ultrasonic element emission group 35 is designated as S3. The ultrasonic element emission group 35 to be the first emission unit S1 includes ultrasonic elements 31 in a section ranging from the first to third columns from one end in the length direction. The ultrasonic element emission group 35 to be the second emission unit S2 includes ultrasonic elements 31 in a section ranging from the second to fourth columns from one end in the length direction. The ultrasonic element emission group 35 to be the emission unit S3 includes ultrasonic elements 31 in a section ranging from the third to fifth columns from one end in the length direction. In other words, the probe 21 emits ultrasonic waves a large number of times while changing the position of the emission unit in the length direction by only one row of ultrasonic elements 31 arranged in the width direction, thereby emitting ultrasonic waves over the entire length in the length direction.

The control unit 25 is connected to the probe 21 and controls the probe 21, thereby controlling the emission of ultrasonic waves emitted from the array of ultrasonic elements 31. Specifically, the control unit 25 simultaneously excites the certain of ultrasonic elements 31 in the ultrasonic element emission group 35, thereby emitting (transmitting) ultrasonic waves from the probe 21 in the emission unit corresponding to the ultrasonic element emission group 35. Meanwhile, the control unit 25 receives ultrasonic waves reflected by the object to be inspected at each ultrasonic element 31 in the ultrasonic element emission group 35. The control unit 25 obtains flaw detection results for each emission unit on the basis of results received by the respective ultrasonic elements 31 in the ultrasonic element emission group 35. The control unit 25 causes the probe 21 to transceive ultrasonic waves a large number of times while changing the position of the ultrasonic element emission group 35 in the length direction by only one row of ultrasonic elements arranged in the width direction, thereby detecting flaws in the object to be inspected over the entire length of the probe 21 in the length direction.

Also, as illustrated in FIG. 3, the control unit 25 includes a delay circuit 41 that delays the emission timings of the ultrasonic waves to be emitted from the respective ultrasonic elements 31. In FIG. 3, the array of ultrasonic elements 31 in the ultrasonic element emission group 35 are illustrated, and the delay circuit 41 corresponding to the ultrasonic elements 31 is illustrated. The control unit 25 executes delay control to focus ultrasonic waves on a focal point position P1, a focal point position P2, and a focal point position P3 at predetermined depths inside the object to be inspected in the depth direction, which is orthogonal to the surface to be inspected to which ultrasonic waves are emitted. The focal point position P2 is a focal point in a shallow position in the depth direction, the focal point position P3 is a focal point in a deep position in the depth direction, and the focal point position P1 is a focal point between the focal point position P2 and the focal point position P3. In the first reference example, the ultrasonic waves are focused on the three focal point positions P1, P2, and P3, but there is no special limitation on the depth and number of focal point positions.

With respect to the emission of ultrasonic waves from at least one of the ultrasonic elements 31 in the ultrasonic element emission group 35, the control unit 25 delays the emission of ultrasonic waves to be emitted from other ultrasonic elements 31 using the delay circuit 41. In the first reference example, the control unit 25 delays the emission timing of ultrasonic waves emitted from one central ultrasonic element 31 among the nine ultrasonic elements 31 constituting the ultrasonic element emission group 35, compared to the emission timing of ultrasonic waves emitted from the surrounding eight ultrasonic elements 31. In this manner, the control unit 25 performs delay control using the delay circuit 41, which enables so-called electronic focusing in which the ultrasonic waves are focused. Thus, the ultrasonic element 31 is not provided with a physical focusing mechanism, and the transceiving surface 30 of the probe 21 is flat. The control unit 25 detects flaws in the object to be inspected while switching between the three focal point positions P1, P2, and P3 to obtain the results of flaw detection of the object to be inspected at the focal point position P1, the results of flaw detection of the object to be inspected at the focal point position P2, and the results of flaw detection of the object to be inspected at the focal point position P3. Thus, the ultrasonic testing apparatus 1 can perform ultrasonic flaw detection by switching between the focal point positions P1, P2, and P3, enabling improvement in detection of flaws inside the object to be inspected.

As described above, according to the configuration of the first reference example, it is possible to form the ultrasonic elements 31 so as to have the same length in the length direction and the width direction, and thus, even if the surface to be inspected facing the ultrasonic element 31 is inclined, it is possible to achieve a small difference in height between one end and the other end in the width direction. As a result, it is possible to reduce variation in distance between the ultrasonic element 31 and the surface to be inspected in the width direction, and to stably emit ultrasonic waves to the surface to be inspected.

According to the configuration of the first reference example, it is possible to emit ultrasonic waves a large number of times in the length direction in the emission unit corresponding to the ultrasonic element emission group 35. In this manner, the ultrasonic element emission group 35 makes it possible to increase acoustic pressure compared to a case in which ultrasonic waves are emitted from one ultrasonic element 31, enabling more stable emission of ultrasonic waves, and enabling the ultrasonic waves reflected by the object to be inspected to be more suitably received. Furthermore, the ultrasonic waves can be received by the respective ultrasonic elements 31, and thus, the ultrasonic waves reflected by the object to be inspected can be received in detail.

According to the configuration of the first reference example, if simultaneously exciting a certain of ultrasonic elements 31, the control unit 25 can delay the emission timing of ultrasonic waves emitted from one central ultrasonic element 31, compared to the emission timing of ultrasonic waves emitted from the surrounding eight ultrasonic elements 31. Thus, the control unit 25 can achieve so-called electronic focusing in which the ultrasonic waves are focused on a focal point position P. Focusing the ultrasonic waves in this manner makes it possible to increase acoustic pressure and improve resolution, enabling improvement in sensitivity in ultrasonic flaw detection.

Also, according to the configuration of the first reference example, the control unit 25 emits, throughout the length direction of the probe 21, ultrasonic waves a large number of times with the respective portions of the emission units overlapping, thereby emitting ultrasonic waves at a short interval. As a result, it is possible to perform precise ultrasonic flaw detection in the length direction.

Embodiment

Figure 4:
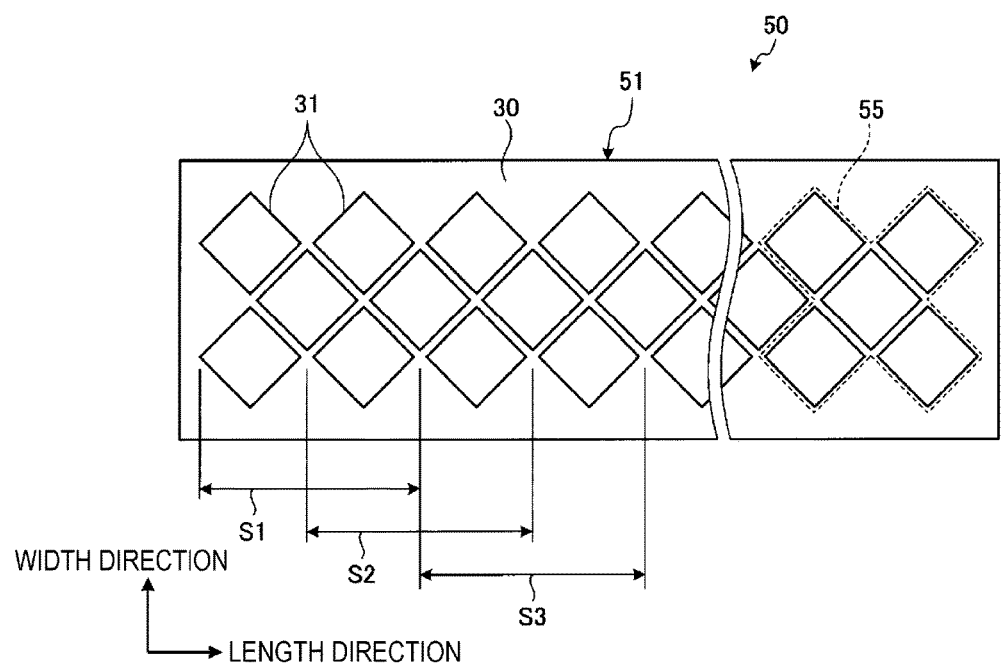
FIG. 4 is a schematic diagram illustrating a transceiving surface of a probe of an ultrasonic testing apparatus according to at least one embodiment.

Next, description will be given of an ultrasonic testing apparatus 50 according to the embodiment with reference to FIG. 4. FIG. 4 is a schematic diagram illustrating a transceiving surface of a probe of the ultrasonic testing apparatus according to the embodiment. In the embodiment, in order to avoid repeating the description in the first reference example, description will be given only of portions differing from the first reference example, and the same reference numerals will be used for the description of the same portions as the first reference example.

The probe 51 of the ultrasonic testing apparatus 50 of the embodiment is of a matrix array type, and is provided with an array of ultrasonic elements 31 arranged on a transceiving surface 30 so as to be inclined at a predetermined angle relative to the length direction and the width direction. Here, the predetermined angle is 45°, for example, and the array of ultrasonic elements 31 are provided in a direction inclined at 45° to the length direction and in a direction inclined at 45° to the width direction. Each ultrasonic element 31 is formed such that the lengths in the length direction and width direction are the same in a manner similar to the first reference example, and is formed in a square shape in the embodiment as well. The array of ultrasonic elements 31 are arranged such that groups of three ultrasonic elements 31 arranged in a direction inclined at 45° to the length direction are arranged in the length direction while being shifted by the length of one ultrasonic element 31 at a time in the direction inclined at 45° to the length direction, for example. Thus, the array of ultrasonic elements 31 is arranged in the length direction in an X-shaped arrangement. The probe 51 emits, throughout the length direction thereof, ultrasonic waves a large number of times in a predetermined emission unit.

The emission unit corresponds to an ultrasonic element emission group 55 surrounded by the dotted line in FIG. 4. In other words, the ultrasonic element emission group 55 is constituted of a total of five ultrasonic elements, with one ultrasonic element being surrounded by two ultrasonic elements 31 adjacent to each other in the length direction on a diagonal line of the ultrasonic elements 31 and two ultrasonic elements 31 adjacent to each other in the width direction on a diagonal line of the ultrasonic elements 31. In other words, the ultrasonic element emission group 55 is constituted of a total of five ultrasonic elements 31: one ultrasonic element 31 positioned in the width direction center, and four ultrasonic elements 31 adjacent to the four sides of the central ultrasonic element 31. If emitting ultrasonic waves with such an ultrasonic element emission group 55 as the emission unit, the probe 51 emits ultrasonic waves a large number of times while changing the position of the emission unit in the length direction from one end to the other end in the length direction with the respective portions of the emission units overlapping.

Specifically as illustrated in FIG. 4, the first emission unit as the ultrasonic element emission group 55 is designated as S1, the second emission unit as the ultrasonic element emission group 55 is designated as S2, and the third emission unit as the ultrasonic element emission group 55 is designated as S3. The ultrasonic element emission group 55 to be the first emission unit S1 uses the ultrasonic element 31 in the width direction center located on one side in the length direction and four ultrasonic elements 31 adjacent to the four sides of the ultrasonic element 31 in the width direction center. The ultrasonic element emission group 55 to be the second emission unit S2 uses the ultrasonic element 31 in the width direction center adjacent, on the other side in the length direction, to the ultrasonic element 31 in the width direction center of the emission unit S1, and four ultrasonic elements 31 adjacent to the four sides of the ultrasonic element 31 in the width direction center. At this time, among the five ultrasonic elements 31 of the emission unit S1, two ultrasonic elements 31 adjacent to two sides on the other side in the length direction of the ultrasonic element 31 in the width direction center are the same as two ultrasonic elements 31 adjacent to two sides on the one side in the length direction of the ultrasonic element 31 in the width direction center among five ultrasonic elements 31 of the emission unit S2. The ultrasonic element emission group 55 to be the third emission unit S3 uses the ultrasonic element 31 in the width direction center adjacent, on the other side in the length direction, to the ultrasonic element 31 in the width direction center of the emission unit S2, and four ultrasonic elements 31 adjacent to the four sides of the ultrasonic element 31 in the width direction center. At this time, among five ultrasonic elements 31 of the emission unit S2, two ultrasonic elements 31 adjacent to two sides on the other side in the length direction of the ultrasonic element 31 in the width direction center are the same as two ultrasonic elements 31 adjacent to two sides on the one side in the length direction of the ultrasonic element 31 in the width direction center among five ultrasonic elements 31 of the emission unit S3. In other words, the probe 51 emits ultrasonic waves a large number of times throughout the length direction of the probe 51 with an overlap of two ultrasonic elements 31 in the ultrasonic element emission groups 55, thereby emitting ultrasonic waves over the entire length in the length direction.

The control unit 25 is connected to the probe 51, and, similar to the first reference example, simultaneously excites the certain of ultrasonic elements 31 in the ultrasonic element emission group 55, thereby performing emission control in which ultrasonic waves are emitted from the probe 51 in the emission unit corresponding to the ultrasonic element emission group 55. Also, the control unit 25 receives ultrasonic waves reflected by the object to be inspected at each of the ultrasonic elements 31 in the ultrasonic element emission group 55. The control unit 25 causes the probe 51 to transceive ultrasonic waves a large number of times with an overlap of two ultrasonic elements 31 in the ultrasonic element emission groups 55, thereby detecting flaws in the object to be inspected over the entire length of the probe 51 in the length direction.

Also, the control unit 25 delays the emission timing of the ultrasonic waves from the respective ultrasonic elements 31 in the ultrasonic element emission group 55 illustrated in FIG. 4. In the embodiment, the control unit 25 delays the emission timing of ultrasonic waves emitted from the ultrasonic element 31 in the width direction center among the five ultrasonic elements 31 constituting the ultrasonic element emission group 55 illustrated in FIG. 4, compared to the emission timing of ultrasonic waves emitted from the four ultrasonic elements 31 adjacent to the four sides of the central ultrasonic element 31. In this manner, the control unit 25 can achieve, through this delay control, so-called electronic focusing in which the ultrasonic waves are focused. Thus, even in the embodiment, the ultrasonic element 31 is not provided with a physical focusing mechanism, and the transceiving surface 30 of the probe 51 is flat.

As described above, according to the configuration of the embodiment, it is possible to emit ultrasonic waves a large number of times throughout the length direction in the emission unit corresponding to the ultrasonic element emission group 55. In this manner, the ultrasonic element emission group 55 makes it possible to increase acoustic pressure compared to a case in which ultrasonic waves are emitted from one ultrasonic element 31, enabling more stable emission of ultrasonic waves, and enabling the ultrasonic waves reflected by the object to be inspected to be more suitably received. Furthermore, the ultrasonic waves can be received by the respective ultrasonic elements 31, and thus, the ultrasonic waves reflected by the object to be inspected can be received in detail.

Even in the configuration of the embodiment, changing emission timings for ultrasonic waves emitted from the certain of ultrasonic elements 31 in the ultrasonic element emission group 55 makes it possible to achieve so-called electronic focusing in which ultrasonic waves are focused on a predetermined focal point position P. Thus, focusing the ultrasonic waves in this manner makes it possible to increase acoustic pressure and improve resolution, enabling improvement in sensitivity in ultrasonic flaw detection.

Also, even with the configuration of the embodiment, the control unit 25 emits, throughout the length direction of the probe 51, ultrasonic waves a large number of times with the respective portions of the emission units overlapping, thereby emitting ultrasonic waves at a short interval. As a result, it is possible to perform precise ultrasonic flaw detection in the length direction.

Second Reference Example

Figure 5:
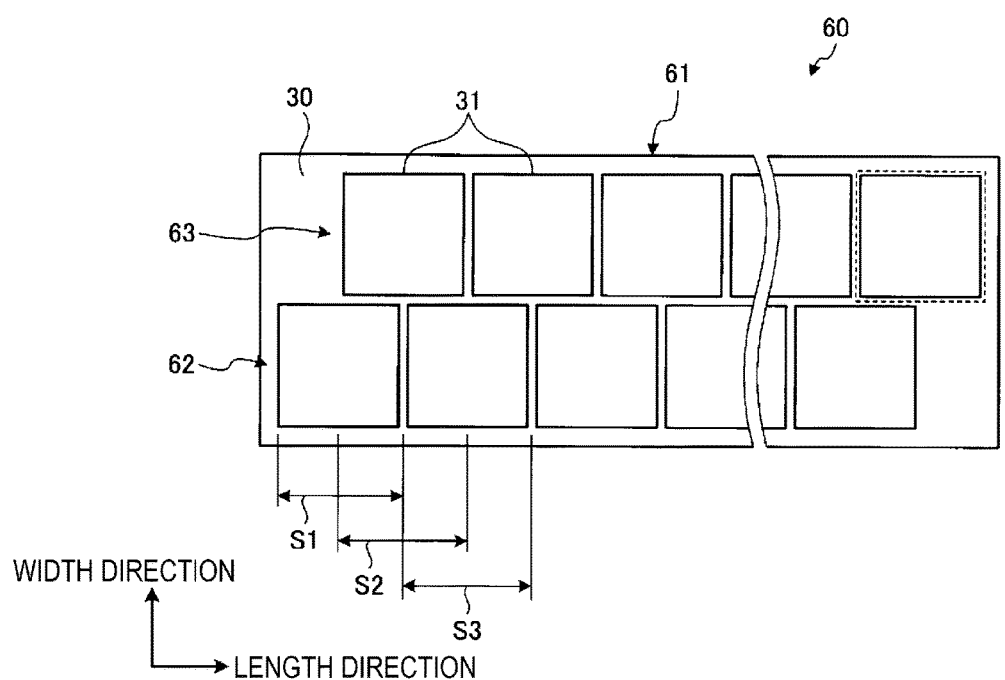
FIG. 5 is a schematic diagram illustrating a transceiving surface of a probe of an ultrasonic testing apparatus according to a second reference example.

Next, description will be given of an ultrasonic testing apparatus 60 according to the second reference example with reference to FIG. 5. FIG. 5 is a schematic diagram illustrating a transceiving surface of a probe of the ultrasonic testing apparatus according to the second reference example. Here, in the second reference example, in order to avoid repeating the description the first reference example, description will be given only of portions different from the first reference example and the same reference numerals will be used for the description of the same portions as the first reference example.

A probe 61 of the ultrasonic testing apparatus 60 of the second reference example is provided with an array of ultrasonic elements 31 arranged in the length direction and the width direction. Each ultrasonic element 31 is formed such that the lengths in the length direction and width direction are the same in a manner similar to the first reference example, and is formed in a square shape in the second reference example as well. Here, the ultrasonic element 31 of the second reference example is larger than the ultrasonic element 31 of the first reference example. Specifically, the array of ultrasonic elements 31 include a first ultrasonic element group 62 arranged in one row in the length direction, and a second ultrasonic element group 63 arranged in one row in the length direction, the second ultrasonic element group 63 being adjacent in the width direction to the first ultrasonic element group 62. Each of the ultrasonic elements 31 in the first ultrasonic element group 62 is positioned between ultrasonic elements 31 in the second ultrasonic element group 63 that are adjacent to each other in the length direction. Thus, the array of ultrasonic elements 31 has a staggered arrangement in the length direction. The probe 61 emits, throughout the length direction thereof, ultrasonic waves a large number of times in a predetermined emission unit.

The emission unit is one ultrasonic element 31 surrounded by the dotted line in FIG. 5. To emit ultrasonic waves with such an ultrasonic element 31 as the emission unit, the probe 61 emits ultrasonic waves a large number of times while changing the position of the emission unit from one end to the other end in the length direction.

Specifically as illustrated in FIG. 5, the first emission unit of the ultrasonic element 31 is designated as S1, the second emission unit of the ultrasonic element 31 is designated as S2, and the third emission unit of the ultrasonic element 31 is designated as S3. The ultrasonic element 31 to be the first emission unit S1 is the first ultrasonic element 31 in the first ultrasonic element group 62 on one side in the length direction. The ultrasonic element 31 to be the second emission unit S2 is the first ultrasonic element 31 in the second ultrasonic element group 63 on the one side in the length direction. The ultrasonic element 31 to be the emission unit S3 is the second ultrasonic element 31 in the first ultrasonic element group 62 on the one side in the length direction. At this time, the ultrasonic element 31 in the emission unit S2 is positioned between the ultrasonic element 31 in the emission unit S1 and the ultrasonic element 31 in the emission unit S3, in the length direction. In other words, the probe 61 emits ultrasonic waves a large number of times while switching alternately between an ultrasonic element 31 in the first ultrasonic element group 62 and an ultrasonic element 31 in the second ultrasonic element group 63 in the length direction, thereby emitting ultrasonic waves over the entire length in the length direction.

The control unit 25 is connected to the probe 61 and performs emission control in which ultrasonic waves are emitted from the probe 61 with one ultrasonic element 31 as an emission unit. Also, the control unit 25 receives ultrasonic waves reflected by the object to be inspected at the one ultrasonic element 31 that has emitted ultrasonic waves. Furthermore, the control unit 25 causes the probe 21 to transceive ultrasonic waves a large number of times while switching alternately between the ultrasonic element 31 in the first ultrasonic element group 62 and the ultrasonic element 31 in the second ultrasonic element group 63 in the length direction, thereby detecting flaws in the object to be inspected over the entire length of the probe 61 in the length direction.

In the second reference example, the emission unit corresponds to one ultrasonic element 31, which does not allow electronic focusing. Thus, a physical focusing mechanism may be provided on the transceiving surface 30 of the probe 61.

As described above, according to the configuration of the second reference example, it is possible to emit ultrasonic waves a large number of times throughout the length direction in the emission unit corresponding to one ultrasonic element 31. At this time, the ultrasonic elements 31 in the first ultrasonic element group 62 and the ultrasonic elements 31 in the second ultrasonic element group 63 can alternately emit ultrasonic waves along the length direction. Thus, ultrasonic waves can be emitted at a shorter interval than the respective intervals between the ultrasonic elements 31 in the ultrasonic element group 62 and between the ultrasonic elements 31 in the ultrasonic element group 63, enabling precise ultrasonic wave flaw detection along the length direction.

The invention claimed is:

1. A probe comprising:
   a transceiving surface that has a greater length in a length direction than in a width direction; and
   a plurality of ultrasonic elements provided on the transceiving surface;
   the probe emitting ultrasonic waves to a surface to be inspected of an object to be inspected, the surface to be inspected facing the transceiving surface, while moving in the width direction, wherein
   each of the ultrasonic elements is formed in a square shape;
   wherein a center row of ultrasonic elements is arranged in the length direction in a center of the width direction, and is disposed such that each side of the ultrasonic element is tilted by 45 degrees with respect to the length direction, and further ultrasonic elements are arranged adjacent to each side of the ultrasonic elements in the center row, the further ultrasonic elements being disposed substantially similarly to the ultrasonic elements in the center row, and the probe being further arranged to:
   emit ultrasonic waves from an emission unit that includes one ultrasonic element of the center row of ultrasonic elements and four ultrasonic elements of the further ultrasonic elements adjacent to the one ultrasonic element; and
   shift the emission unit by one ultrasonic element in the length direction such that each of the further ultrasonic elements emits ultrasonic waves twice and each of the ultrasonic elements of the center row emits ultrasonic waves once.

2. An ultrasonic testing apparatus comprising:
   the probe according to claim 1; and
   a control unit that is configured to control the probe, wherein
   the control unit is further configured to perform emission control to emit ultrasonic waves from the emission unit.

3. The ultrasonic testing apparatus according to claim 2, wherein
   the control unit is further configured to simultaneously excite ultrasonic elements in the emission unit to emit ultrasonic waves, wherein the ultrasonic elements are further configured to receive ultrasonic waves reflected by the object to be inspected at each of the ultrasonic elements.

4. The ultrasonic testing apparatus according to claim 3, wherein
   the control unit is further configured to perform delay control to delay emission of the ultrasonic waves emitted from the ultrasonic element arranged in the center of the emission unit with respect to emission of the ultrasonic waves from the other ultrasonic elements in the emission unit.

5. An ultrasonic testing apparatus comprising:
   the probe according to claim 1; and
   a control unit that controls the probe.

6. An ultrasonic testing control method for controlling a probe, the probe including a transceiving surface that has a greater length in a length direction than in a width direction, and a plurality of ultrasonic elements provided on the transceiving surface, the probe emitting ultrasonic waves to a surface to be inspected of an object to be inspected, the surface to be inspected facing the transceiving surface, while moving in the width direction, wherein
   each of the ultrasonic elements is formed in a square shape,
   wherein a center row of ultrasonic elements are arranged in the length direction in a center of the width direction, and are disposed such that each side of the ultrasonic element is tilted by 45 degrees with respect to the length direction, and further ultrasonic elements are arranged adjacent to each side of the ultrasonic elements in the center row, the further ultrasonic elements being disposed substantially similarly to the ultrasonic elements in the center row, the method comprising the steps of:
   emitting ultrasonic waves from an emission unit that includes one ultrasonic element of the center row of ultrasonic elements and four ultrasonic elements of the further ultrasonic elements adjacent to the one ultrasonic element; and
   shifting the emission unit by one ultrasonic element in the length direction such that each of the further ultrasonic elements emits ultrasonic waves twice and each of the ultrasonic elements of the center row emits ultrasonic waves once.

* * * * *